US010059977B2

(12) United States Patent
Witcher et al.

(10) Patent No.: US 10,059,977 B2
(45) Date of Patent: Aug. 28, 2018

(54) BIOLOGICAL STERILIZATION INDICATOR (71) Applicant: 3M INNOVATIVE PROPERTIES COMPANY, St. Paul, MN (US)

(72) Inventors: Kelvin J. Witcher, Hudson, WI (US); William E. Foltz, Cottage Grove, MN (US); Naiyong Jing, St. Paul, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/484,781

(22) Filed: Apr. 11, 2017

(65) Prior Publication Data
US 2017/0218428 A1 Aug. 3, 2017

Related U.S. Application Data (63) Continuation of application No. 14/891,760, filed as application No. PCT/US2014/037829 on May 13, 2014, now Pat. No. 9,650,661.

(60) Provisional application No. 61/825,854, filed on May 21, 2013.

(51) Int. Cl.
    C12Q 1/22 (2006.01)
(52) U.S. Cl.
    CPC .................... C12Q 1/22 (2013.01)
(58) Field of Classification Search
    IPC .................. C12N 11/06; C12Q 1/22
    See application file for complete search history.

(56) References Cited

U.S. PATENT DOCUMENTS

| | | | |
|---|---|---|---|
| 2,366,516 A | 1/1945 | Geffcken et al. | |
| 2,432,484 A | 12/1947 | Moulton | |
| 2,536,764 A | 1/1951 | Moulton | |
| 2,601,123 A | 6/1952 | Moulton | |
| 3,846,242 A | 11/1974 | Ernst | |
| 4,717,661 A | 1/1988 | McCormick et al. | |
| 4,816,333 A | 3/1989 | Lange et al. | |
| 5,039,561 A | 8/1991 | Debe | |
| 5,073,488 A | 12/1991 | Matner et al. | |
| 5,223,401 A | 6/1993 | Foltz et al. | |
| 5,418,167 A | 5/1995 | Matner et al. | |
| 5,585,186 A | 12/1996 | Scholz et al. | |
| 5,723,175 A | 3/1998 | Scholz et al. | |
| 5,739,004 A | 4/1998 | Woodson | |
| 5,753,373 A | 5/1998 | Scholz et al. | |
| 5,795,730 A | 8/1998 | Tautvydas | |
| 6,040,053 A | 3/2000 | Scholz et al. | |
| 6,326,723 B1 | 12/2001 | Raj et al. | |
| 6,386,699 B1 | 5/2002 | Ylitalo et al. | |
| 6,420,622 B1 | 7/2002 | Johnston et al. | |
| 6,867,342 B2 | 3/2005 | Johnston et al. | |
| 7,140,812 B2 | 11/2006 | Bryan et al. | |
| 7,143,709 B2 | 12/2006 | Brennan et al. | |
| 7,223,364 B1 | 5/2007 | Johnston et al. | |
| 7,309,519 B2 | 12/2007 | Scholz et al. | |
| 7,416,883 B2 | 8/2008 | Cregger et al. | |
| 7,476,533 B2 | 1/2009 | Meathrel et al. | |
| 7,678,426 B2 | 3/2010 | Flynn et al. | |
| 7,879,746 B2 | 2/2011 | Klun et al. | |
| 7,960,169 B2 | 6/2011 | Cregger et al. | |
| 9,383,294 B2 | 7/2016 | Kenney et al. | |
| 9,650,661 B2 * | 5/2017 | Witcher | C12Q 1/22 |
| 2002/0008461 A1 | 1/2002 | Raj et al. | |
| 2002/0128578 A1 | 9/2002 | Johnston et al. | |
| 2003/0129087 A1 | 7/2003 | Barbee, Jr. et al. | |
| 2003/0235677 A1 | 12/2003 | Hanschen et al. | |
| 2005/0089539 A1 | 4/2005 | Scholz et al. | |
| 2006/0024508 A1 | 2/2006 | D'Urso et al. | |
| 2006/0051384 A1 | 3/2006 | Scholz et al. | |
| 2006/0051385 A1 | 3/2006 | Scholz | |
| 2006/0052452 A1 | 3/2006 | Scholz | |
| 2006/0057307 A1 | 3/2006 | Matsunaga et al. | |
| 2006/0083657 A1 | 4/2006 | McDonnell et al. | |
| 2007/0134784 A1 | 6/2007 | Halverson et al. | |
| 2007/0231542 A1 | 10/2007 | Deng et al. | |
| 2007/0298216 A1 | 12/2007 | Jing et al. | |
| 2008/0044850 A1 | 2/2008 | Taylor et al. | |
| 2008/0090010 A1 | 4/2008 | Zhang et al. | |
| 2008/0107864 A1 | 5/2008 | Zhang et al. | |
| 2010/0035039 A1 | 2/2010 | Jing et al. | |

(Continued)

FOREIGN PATENT DOCUMENTS

| CA | 2 323 719 | 4/2001 |
|---|---|---|
| DE | 198 18 956 | 11/1998 |

(Continued)

OTHER PUBLICATIONS

Ling, C. et al. Fabrication of Carbon Nanotube/Graphene Core/Shell Nanostructures on SiO2 Substrates Using Organic Solvents. Chinese Science Bulletin 57(23)3030-3035, Aug. 2012. (Year: 2012).*

Mohammadipanah, F. et al. Efficacy of Nanostructures as Preservation Carriers of Bacillus atrophaeus in the Preparation of Sterilization Bioindicators. J Pharmaceutical Innovation 11(4)323-330, Dec. 2016. (Year: 2016).*

Barthlott, W. et al.; "Purity of the sacred lotus, or escape from contamination in biological surfaces" Planta vol. 202; (1997); pp. 1-8.

Bernhard, C.G. et al.; "A Corneal Nipple Pattern in Insect Compound Eyes"; Acta physiol. Scand.; vol. 56; (1962); pp. 385-386.

Blossey, R.; "Self-cleaning surfaces—virtual realities"; Nature Materials; vol. 2; (2003); pp. 301-306.

Bragg, W.L. et al.; "The Form Birefringence of Macromolecules"; Acta Cryst;; vol. 6; (1953); pp. 865-867.

Busscher, H.J. et al.; "Adhesion and Spreading of Human Fibroblasts on Superhydrophobic Fep-Teflon"; Cells and Materials; vol. 1, No. 3; (1991); pp. 243-249).

Callow, M.E. et al.; "Marine biofouling: a sticky problem"; Biologist; vol. 49, No. 1; (2002); pp. 10-14.

Cao, F. et al.; "Preparation of Material Surface Structure Similar to Hydrophobic Structure of Lotus Leaf"; Journal of Wuhan of Technology-Mater. Sci. Ed.; (2008); pp. 513-517.

Carman, M.L. et al.; "Engineered antifouling microtopograpies—correlating wettability with cell attachment"; Biofouling; vol. 22; No. 1; (2006); pp. 11-21.

(Continued)

Primary Examiner — Ralph J Gitomer
(74) Attorney, Agent, or Firm — 3M Innovative Properties Company; Carlos M. Téllez (57) ABSTRACT

Spore carriers suitable for use in biological indicators are described. The spore carriers include a substrate such as polymeric film or non-woven web with a hydrophilic nanostructured layer bonded to it. Spores are bonded to the nanostructured layer. Nanostructured layers including nanoparticles, such as acid-sintered silica nanoparticles are described. Biological indicators including such spore carriers are also described.

20 Claims, 2 Drawing Sheets

(56) References Cited

U.S. PATENT DOCUMENTS

| | | |
|---|---|---|
| 2010/0092765 A1 | 4/2010 | Hager et al. |
| 2010/0226943 A1 | 9/2010 | Brennan et al. |
| 2012/0276369 A1 | 11/2012 | Jing et al. |
| 2013/0210048 A1 | 8/2013 | Chandrapati et al. |
| 2015/0017386 A1 | 1/2015 | Kolb et al. |

FOREIGN PATENT DOCUMENTS

| | | |
|---|---|---|
| DE | 199 50 452 | 4/2001 |
| JP | 2008-2007 | 1/2008 |
| JP | 2010-512516 | 4/2010 |
| WO | WO 2004/000569 | 12/2003 |
| WO | WO 2005/111193 | 11/2005 |
| WO | WO 2007/070310 | 6/2007 |
| WO | WO 2007/075390 | 7/2007 |
| WO | WO 2008/070625 | 6/2008 |
| WO | WO 2008/070865 | 6/2008 |
| WO | WO 2009/152345 | 12/2009 |
| WO | WO 2009/158046 | 12/2009 |
| WO | WO 2010/039388 | 4/2010 |
| WO | WO 2011/062880 | 5/2011 |
| WO | WO 2011/150103 | 12/2011 |
| WO | WO 2012/058605 | 5/2012 |
| WO | WO 2012/061212 | 5/2012 |
| WO | WO 2012/078374 | 6/2012 |
| WO | WO 2013/066874 | 5/2013 |

OTHER PUBLICATIONS

Castner, D.G. et al.; "Biomedical surface science: Foundations to frontiers"; Surface Science; vol. 500; (2002); pp. 28-60.

Chen, W. et al.; "Ultrahydrophobic and Ultralyophobic Surfaces: Some Comments and Examples"; Langmuir; vol. 15; (1999); pp. 3395-3399.

Cheng, Y. et al.; "Microscopic observations of condensation of water on lotus leaves"; Applied Physics Letters; vol. 87; (2005); pp. 194112-1-194112-2.

Choong, S. et al.; "Catheter associated urinary tract infection and encrustation"; International Journal of Antimicrobial Agents vol. 17; (2001); pp. 305-310.

Chung, K.K. et al.; "Impact of engineered surface microtopography on biofilm formation of *Staphylococcus aureus*"; Biointerphases; vol. 2, No. 2; (2007); pp. 89-94.

Costerton, J.W. et al.; "How Bacteria Stick—In nature (but not in laboratory cultures) bacteria are covered by a "glycocalyx" of fibers that adhere to surfaces and to other cells. Adhesion might be prevented by a new kind of antibiotic"; Sci. Am;; vol. 238; (1978); pp. 86-95.

Costerton, J.W. et al.; "Microbial Biofilms"; Annu. Rev. Microbiol.; vol. 49; (1995); pp. 711-745.

Costerton, J.W. et al.; "Bacterial Biofilms: A Common Cause of Persistent Infections"; Science; vol. 284; (1999); pp. 1318-1322.

Costerton, W. et al.; "The application of biofilm science to the study and control of chronic bacterial infections"; The Journal of Clinical Investigation; vol. 112, No. 10; (2003); pp. 1466-1477.

Doshi, P. et al.; "Characterization and optimization of absorbing plasma-enhanced chemical vapor deposited antireflection coatings for silicon photovoltaics"; Applied Optics; vol. 36, No. 30; (1997); pp. 7826-7837.

Erbil, H.Y. et al.; "Transformation of a Simple Plastic into a Superhydrophobic Surface"; Science; vol. 299; (2003); pp. 1377-1380.

Feng, L. et al.; "Super-Hydrophobic Surfaces: From Natural to Artificial**"; Advanced Materials' vol. 14, No. 24; (2002); pp. 1857-1860.

Fux, C.A. et al.; "Survival strategies of infectious biofilms"; Trends in Microbiology; vol. 13, No. 1; (2005); pp. 34-40.

Gao, L. et al.; ""Artificial Lotus Leaf"Prepared Using a 1945 Patent and a Commercial Textile"; Langmuir; vol. 22; (2006); pp. 5998-6000.

Gombert, A. et al.; "Subwavelength-structured antireflective surfaces on glass"; Thin Solid Films; vol. 351; (1999); pp. 73-78.

Hadobás, K. et al.; "Reflection properties of nanostructure-arrayed silicon surfaces"; Nanotechnology; vol. 11; (2000); pp. 161-164.

Hall-Stoodley, L. et al.; "Bacterial Biofilms: From the Natural Environment to Infectious Diseases"; Nature Reviews Microbiology; vol. 2; (2004); pp. 98-108.

Henoch, C. et al.; "Turbulent Drag Reduction Using Superhydrophobic Surfaces"; 3rd American Institute of Aeronautics and Astronautics Flor Control Conference Jun. 5-8, 2006, San Francisco, California; (AIAA 2006-3192); pp. 1-5.

Huang, Y. et al.; "Improved broadband and quasi-omnidirectional anti-reflection properties with biomimetic silicon nanostructures"; Nature Technology; vol. 2; (2007); pp. 770-774.

Jin, M. et al.; "Superhydrophobic Aligned Polystyrene Nanotube Films with High Adhesive Force"; Advanced Materials; vol. 17; (2005); pp. 1977-1981.

Kasugai, H. et al; "High-Efficiency Nitride-Based Light-Emitting Diodes with Moth-Eye Structure"; Japanese Journal of Applied Physics; vol. 44, No. 10; (2005); pp. 7414-7417.

Kim, Y.K. et al.; "Focused Ion Beam Nanopatterning for Optoelectronic Device Fabrication"; IEEE Journal of Selected Topics in Quantum Electronics; vol. 11, No. 6; (2005); pp. 1292-1298.

Kobayashi, H. et a.; "Self-assembly of Fine Particles Applied to the Production of Antireflective Surfaces"; International Journal of Precision Engineering and Manufacturing; vol. 9 No. 1; (2008); pp. 25-29.

Koo, H.Y. et al.; "A Snowman-like Array of Colloidal Dimers for Antireflecting Surfaces"; Advanced Materials; vol. 16, No. 3; (2004); pp. 274-277.

Kuo, C.J. et al.; "Optimization of the Electron-Beam-Lithography Parameters for the Moth-Eye Effects of an Antireflection Matrix Structure"; Journal of Applied Polymer Science; vol. 102; (2006); pp. 5303-5313.

Li, X et al.; "What do we need for a superhydrophobic surface? A rview on the recent progress in the preparation of superhydrophobic surfaces"; Chem Soc. Rev.; vol. 36; (2007); pp. 1350-1368 (XP-002667653).

Linn, N.C. et al.; "Self-assembled biomimetic antireflection coatings"; Applied Physics Letters; vol. 91; (2007); pp. 101108-1-101108-3.

Min, W. et al.; "Bioinspired Self-Cleaning Antireflection Coatings**"; Advanced Materials; vol. 20; (2008); pp. 1-5.

Min, W. et al.; "Large-scale assembly of colloidal nanoparticles and fabrication of periodic subwavelength structures"; Nanotechnology; vol. 19; (2008); 475604 (7 pgs).

Misra, R. et al.; "Nonwetting, Nonrolling, Stain Resistant Polyhedral Oligomeric Silsesquioxane Coated Textiles"; Journal of Applied Polymer Science; vol. 115; (2010); pp. 2322-2331.

Nishino, T. et al.; "The Lowest Surface Free Energy based on $-CF_3$ Alignment"; Langmuir; vol. 15; (1999); pp. 4321-4323.

Oner, D. et al.; "Ultrahydrophobic Surfaces. Effects of Topography Length Scales on Wettability"; Langmuir; vol. 16; (2000); pp. 7777-7782.

Prevo, B.G. et al.; "Assembly and characterization of colloid-based antireflective coatings on multicrystalline silicon solar cells"; Journal of Materials Chemistry; vol. 17; (2007); pp. 791-799.

Qian, B. et al.; "Fabrication of Superhydrophobic Surfaces by Dislocation-Selective Chemical Etching on Aluminum, Copper, and Zinc Substrates"; Langmuir; vol. 21; (2005); pp. 9007-9009.

Sasaki, M. et al.; "Processing and properties of transparent superhydrophobic polymer film with low surface electric resistance"; Journal of Materials Science; vol. 39; (2004); pp. 3717-3722.

Schulz, U.; "Review of modern techniques to generate antireflective properties on thermoplastic polymers"; Applied Optics; vol. 45, No. 7; (2006); pp. 1608-1618.

Schumacher, J.F. et al.; "Engineered antifouling microtopographies—effect of feature size, geometry, and roughness on settlement of zoospores of the green alga *Ulva*"; Biofouling; vol. 23; No. 1; (2007); pp. 55-62.

Schumacher J.F. et al.; "Engineered Nanoforce Gradients for Inhibition of Settlement (Attachment) of Swimming Algal Spores"; Langmuir; vol. 24; (2008); pp. 4931-4937.

(56) References Cited

OTHER PUBLICATIONS

Shibuichi, S. et al.; "Super Water-Repellent Surfaces Resulting from Fractal Structure"; Journal of Physical Chemistry; vol. 100; (1996); pp. 19512-19517.

Stickler, D. J.; "Bacterial biofilms in patients with indwelling urinary catheters"; Nature Clinical Practice Urology; vol. 5, No. 11; (2008); pp. 598-608.

Sun, C. et al.; "Fabrication of super-hydrophobic film with dual-size roughness by silica sphere assembly"; Thin Solid Films; vol. 515; (2007); pp. 4686-4690.

Sun, C. et al.; "Biomimetic subwavelength antireflective gratings on GaAs"; Optics Letters; vol. 33, No. 19; (2008); pp. 2224-2226.

Sun, C. et al.; "Broadband moth-eye antireflection coatings on silicon"; Applied Physics Letters; vol. 92; (2008); pp. 061112-1-061112-3.

Sun, M. et al.; "Artificial Lotus Leaf by Nanocasting"; Langmuir; vol. 21, (2005); pp. 8978-8981.

Takeda, K. et al.; "Preparation of transparent super-hydrophobic polymer film with brightness enhancement property"; Journal of Materials Science Letters; vol. 20; (2001); pp. 2131-2133.

Takeshita, N. et al.; "Simultaneous tailoring of Surface Topography and Chemical Structure for Controlled Wettability"; Langmuir; vol. 20; (2004); pp. 8131-8136.

Tirrell, M. et al.; "The role of surface science in bioengineered materials"; Surface Sciences; vol. 500; (2002); pp. 61-83.

Wu, Z. et al.; "Deformable Antireflection Coatings from Polymer and Nanoparticle Multilayers"; Advanced Materials; vol. 18; (2006); pp. 2699-2702.

Xi, W. et al.; "The preparation of lotus-like super-hydrophobic copper surfaces by electroplating"; Applied Surface Science; vol. 255; (2009); pp. 4836-4839.

Yancey, S.E. et al.; "The influence of void space on antireflection coatings of silica nanoparticle self-assembled films"; Journal of Applied Physics; vol. 99; (2006); pp. 034313-1-034313-10.

Yebra, D.M. et al.; "Antifouling technology—past, present and future steps towards efficient and environmentally friendly antifouling coatings"; Progress in Organic Coatings; vol. 50; (2004); pp. 75-104.

Zhang, L. et al.; "Superhydrophobic Behavior of a Perfluoropolyether Lotus-Leaf-like Topography"; Langmuir; vol. 22; (2006); pp. 8576-8580.

Zhang, X. et al.; "Superhydrophobic Surfaces: From Structural Control to Functional Application"; Journal of Materials Chemistry; vol. 18; (2008); pp. 621-633.

Zhao, J. et al.; "22.7% Efficient Silicon Photovoltaic Modules with Textured Front Surface"; IEEE Transactions on Electron Devices; vol. 46, No. 7; (1999); pp. 1495-1497.

Zhao, J. et al.; "19.8% efficient "honeycomb" textured multicrystalline and 24.4% monocrystalline silicon solar cells"; Applied Physics Letters; vol. 73, No. 14; (1998); pp. 1991-1993.

Zhu, L. et al.; "Tuning wettability and getting superhydrophobic surface by controlling surface roughness with well-designed microstructures"; Sensors and Actuators; vol. A 130-131; (2006); pp. 595-600.

Brochure entitled "Silane Coupling Agents: Connecting Across Boundaries"; From Gelest Inc. (2006); 60 pgs.

Eka: "Colloidal Silica Dispersions Small Particles Add Big Advantages Facts About Colloidal Silica"; retrieved from internet: URL:http://www.hedinger.de/fildeadmin.user_upload/downloads/Chemotecnisch/Eka_Bindzil_folderV2_ENG070425.pdf) ; retrieved on Aug. 18, 2014 (2007) 2 pgs (XP055135177).

* cited by examiner

BIOLOGICAL STERILIZATION INDICATOR

CROSS REFERENCE TO RELATED APPLICATIONS

This application is a continuation of U.S. application Ser. No. 14/891,760, filed Nov. 17, 2015, now U.S. Pat. No. 9,650,661, which is a national stage filing under 35 U.S.C. 371 of PCT/US2014/037829, filed May 13, 2014, which claims priority to U.S. Provisional Patent Application No. 61/825,854, filed May 21, 2013, the disclosures of which are hereby incorporated by reference in their entirety herein.

FIELD

The present disclosure relates to spore carriers such as those used in biological indicators. Specifically, the spore carriers include spores bonded to a hydrophilic nanostructured surface. Biological indicators incorporating such spore carriers are also described.

SUMMARY

Briefly, in one aspect, the present disclosure provides a spore carrier comprising a substrate, a hydrophilic nanostructured layer bonded to the substrate; and spores bonded to nanostructured layer. In some embodiments, the nanostructured layer has a receding contact angle of no greater than 50 degrees as measured by the Contact Angle Method.

In some embodiments, the nanostructured layer comprises nanoparticles, e.g., silica nanoparticles. In some embodiments, the nanoparticles are acid sintered. In some embodiments, the nanoparticles have an average diameter of no greater than 20 nm.

In some embodiments, the nanostructured layer has an RMS roughness of at least 10 nm. In some embodiments, the nanostructured layer has an RMS roughness of no greater than 500 nm. In some embodiments, the nanostructured layer further comprises microparticles. In some embodiments, the nanostructured layer further comprises a binder, e.g., a tetraalkoxysilane.

In some embodiments, the substrate is polymeric substrate, e.g., polyester or polypropylene. In some embodiments, the substrate is a woven or non-woven web. In some embodiments, the substrate is a film.

In some embodiments, the spores comprise at least one of *Geobacillus stearothermophilus* and *Bacillus atrophaeus*.

In another aspect, the present disclosure provides a biological indicator comprising the spore carrier according to any one of the embodiments of the present disclosure.

The above summary of the present disclosure is not intended to describe each embodiment of the present invention. The details of one or more embodiments of the invention are also set forth in the description below. Other features, objects, and advantages of the invention will be apparent from the description and from the claims.

DETAILED DESCRIPTION

Generally, sterilization is defined as the process of completely destroying all viable sources of biological activity, such as microorganisms, including viruses and spores. In a variety of industries, such as health care, processes used to sterilize equipment such as medical devices, instruments and other disposable and non-disposable articles are monitored. For example, hospitals include a sterility indicator with a batch of articles to assay the lethality of the sterilization process. Both biological and chemical sterility indicators have been used.

One standard type of biological sterility indicator includes a known quantity of test microorganisms serving as sources of biological activity. Often, test microorganisms many times more resistant to particular sterilization processes than typical contaminating organisms are selected. For example, *Geobacillus stearothermophilus* (formerly *Bacillus stearothermophilus*) or *Bacillus atrophaeus* (formerly *Bacillus subtilis*) spores have been used. After the indicator is exposed to the sterilization process, the sources of biological activity (e.g., spores) can be incubated in a nutrient medium to determine whether any of the sources survived the sterilization process, with source metabolism and/or growth indicating that the sterilization process was insufficient to destroy all of the sources of biological activity in the sterility indicator. In turn, this may be used to indicate the monitored sterilization process was ineffective.

Figure 1:
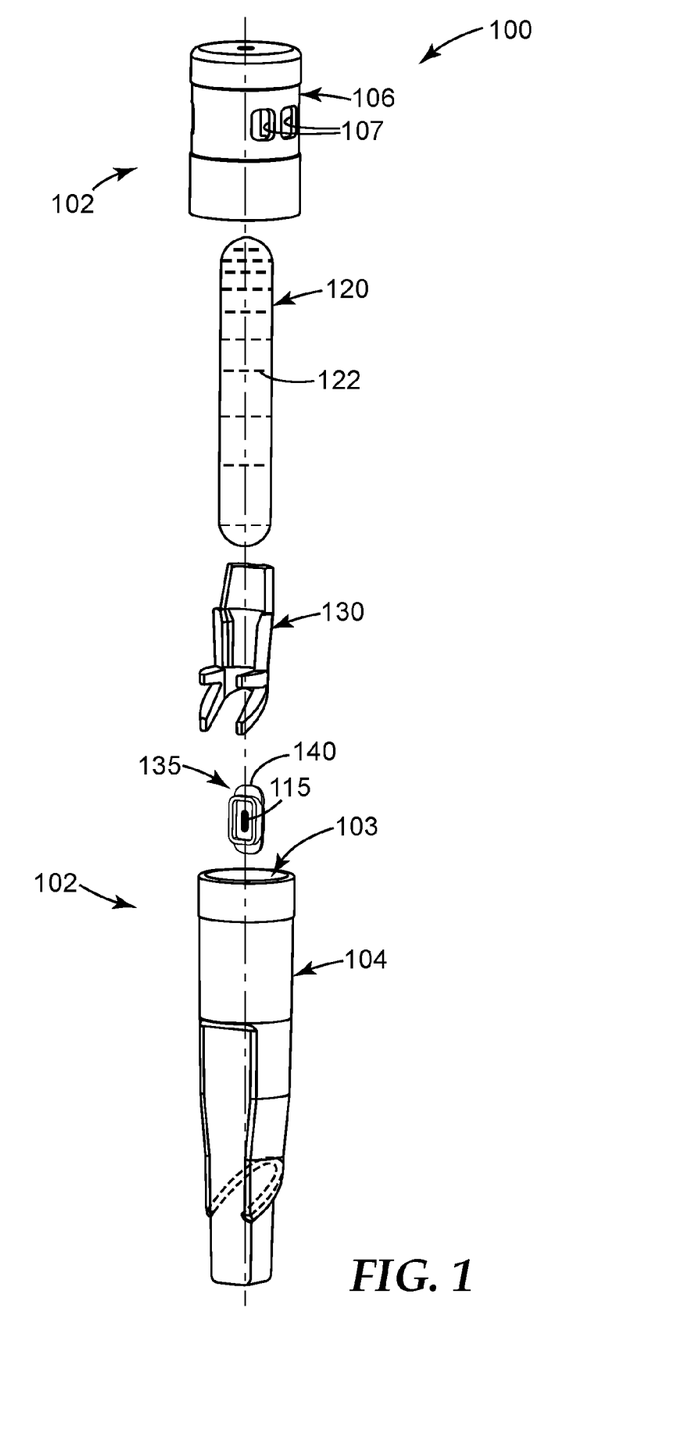
FIG. 1 is an exploded view of an exemplary biological indicator suitable for use in some embodiments of the present disclosure.

Generally, the test microorganisms (e.g., spores) are present on the surface of a substrate. The resulting spore carrier is then integrated into a suitable biological indicator. The spore carriers of the present disclosure may be incorporated into any of a wide variety of known biological indicators. One, non-limiting, exemplary biological indicator is illustrated in FIG. 1.

Generally, biological sterilization indicator 100 includes housing 102 defining reservoir 103 in which other components are located and into which a sterilant can be directed during a sterilization process. In some embodiments, housing 102 comprises base 104 and cap 106 adapted to be coupled together to provide a self-contained biological sterilization indicator. In some embodiments, one-part unitary housings may also be employed. Generally, base 104 and cap 106 are dimensioned to create a reservoir suitable to contain the remaining components of the indicator. Generally, the walls of the housing are liquid impermeable. Suitable materials include, but are not limited to, glass, metal (e.g., foil), polymers (e.g., polyolefins, polycarbonates, polyesters), ceramics, or combinations thereof.

In some embodiments, cap 106 includes one or more apertures 107 to provide fluid communication between the interior of housing 102 and ambience. For example, apertures 107 can provide fluid communication between spores 115 and ambience during a sterilization process. During a sterilization process, ambience may include one or more components suitable to affect sterilization, e.g., steam, ozone, hydrogen peroxide, ethylene oxide, and combinations thereof.

In some embodiments, the biological sterilization indicator includes frangible container 120 containing liquid 122. The frangible container 120 can be formed of a variety of materials, including, but not limited to, one or more of metal (e.g., foil), polymers, glass (e.g., a glass ampoule), and combinations thereof. In some embodiments, only a portion of the container is frangible.

In some embodiments, frangible container 120 is held in place by insert 130, which may be adapted to aid in breaching (e.g., fracturing) the frangible container. Generally, insert 130 holds frangible container 120 separate from spore carrier 135, which comprises spores 115 (or other sources of biological activity) bonded to substrate 140.

Then, when at least a portion of frangible container 120 is breached, liquid 122 becomes in fluid communication with reservoir 103, and contacts spores 115.

The process of bringing the spores and liquid together can be referred to as "activation" of the biological sterilization indicator. That is, the term "activation" and variations thereof, when used with respect to a biological sterilization indicator, can generally refer to bringing one or more sources of biological activity (e.g., spores) in fluid communication with a liquid (e.g., a nutrient medium for the spores of interest). For example, when a frangible container within the biological sterilization indicator that contains the liquid is at least partially fractured, punctured, pierced, crushed, cracked, or otherwise breached, such that the liquid has been put in fluid communication with the source(s) of biological activity, the biological sterilization indicator can be described as having been "activated."

Generally, liquid 122 can include water (or another solvent) that is or can be combined with nutrients to form a nutrient medium. The nutrient medium can generally be selected to induce germination and initial outgrowth of the spores, if viable. The nutrient medium can include one or more sugars, including, but not limited to, glucose, fructose, cellibiose, or the like, or a combination thereof. The nutrient medium can also include a salt, including, but not limited to, potassium chloride, calcium chloride, or the like, or a combination thereof. In some embodiments, the nutrient can further include at least one amino acid, including, but not limited to, at least one of methionine, phenylalanine, and tryptophan.

In some embodiments, liquid 122 can also contain or be combined with indicator molecules or reagents, for example, indicator molecules having optical properties that change in response to germination or growth of the spores. Suitable indicator molecules or reagents can include, but are not limited to, pH indicator molecules (e.g., bromocresol purple (BCP) as shown in the Examples, bromocresol green (BCG), chlorophenol red (CPR), bromthymol blue (BTB), bromophenol blue (BPB), other sulfonphthalein dyes, methyl red, or combinations thereof), enzyme substrates (e.g., 4-methylumbelliferyl-$\alpha$-D-glucoside), DNA binding dyes, RNA binding dyes, other suitable indicator molecules, or a combination thereof. In some embodiments, the combination of bromcresol purple and 4-methylumbelliferyl-alpha-D-glucoside represents an example of a pair of indicator reagents that can be employed together. This combination can be used to detect a first biological activity such as the fermentation of a carbohydrate to acid end products and a second biological activity such as alpha-D-glucosidase enzyme activity, for example. These activities can indicate the presence or absence of a viable spore following the exposure of a biological sterilization indicator to a sterilization process, for example. The bromcresol purple can be used at a concentration of about 0.03 g/L, for example, in an aqueous mixture. The 4-methylumbelliferyl-alpha-D-glucoside can be used, for example, at a concentration of about 0.05 to about 0.5 g/L, for example, in an aqueous mixture.

In some embodiments, the liquid 122 contained within frangible container 120 already includes one or more nutrient media for the spores, such as a germination medium that will promote germination of surviving spores and/or a growth medium to support growth of surviving spores. In some embodiments, the liquid 122 contained within frangible container 120 already includes one or more indicator molecules or reagents. In some embodiments, one or more nutrients necessary to promote germination and/or growth of surviving spores may be provided in a dry form (e.g., powdered form, tablet form, caplet form, capsule form, a film or coating, entrapped in a bead or other carrier, another suitable shape or configuration, or a combination thereof) in the reservoir 103, for example, in a region of the biological sterilization indicator 100 near the spores 115. Similarly, in some embodiments, one or more of the indicator molecules or reagents may be located outside frangible container 120, separate from liquid 122. In such embodiments, when frangible container 120 is breached, liquid 122 incorporates (e.g., dissolves or disperses) the nutrients and/or indicators and contacts the spores, activating the biological indicator.

Generally, the biological sterilization indicator of the present disclosure may include other features or combinations of features generally known in the art. Exemplary features include barriers or filters such as those used to inhibit contaminating foreign organisms, objects or materials from entering the reservoir. Such barriers can include a gas-transmissive, microorganism-impermeable material. During exposure to a sterilant, the sterilant can pass through the barrier into the reservoir and contact the spores. Other elements that may be present include one or more devices or mechanisms suitable to fracture the frangible container at the desired time and in the desired manner. Such devices and mechanisms are well known in the art.

In use, biological sterilization indicators generally keep liquid 122 and spores 115 separate but in relatively close proximity (e.g., within self-contained biological sterilization indicator 100) during sterilization, such that liquid 122 and spores 115 can be readily combined after exposure to a sterilization process. Once activated, liquid 122 and the spores 115 can be incubated prior to or during a detection process. For example, in some embodiments, the incubation temperature is at least about 37° C., in some embodiments, the incubation temperature is at least about 50° C. (e.g., 56° C.), and in some embodiments, at least about 60° C.

Generally, any known detection process may be used to detect a detectable change from the spores 115 depending on other characteristics of the design, e.g., the particular spores and/or indicator molecules or reagents selected. That is, one of ordinary skill in the art could readily select a detection process adapted to detect a variety of characteristics, including, but not limited to, electromagnetic radiation (e.g., in the ultraviolet, visible, and/or infrared bands), fluorescence, luminescence, light scattering, electronic properties (e.g., conductance, impedance, or the like, or combinations thereof), turbidity, absorption, Raman spectroscopy, ellipsometry, or the like, or a combination thereof. Detection of such characteristics can be carried out by one or more of a fluorimeter, a spectrophotometer, colorimeter, or the like, or combinations thereof. In some embodiments, such as embodiments that measure fluorescence, visible light, etc., the detectable change is measured by detecting at a particular wavelength.

The spores 115 and/or the liquid 122 can be adapted (e.g., labeled) to produce one or more of the above characteristics as a result of a biochemical reaction that is a sign of spore viability. As a result, no detectable change (e.g., as compared to a baseline or background reading) can signify an effective sterilization process, whereas a detectable change can signify an ineffective sterilization process. In some embodiments, the detectable change can include a rate at which one or more of the above characteristics is changing (e.g., increasing fluorescence, decreasing turbidity, etc.).

In some embodiments, spore viability can be determined by exploiting enzyme activity. As described in Matner et al., U.S. Pat. No. 5,073,488, entitled "Rapid Method for Determining Efficacy of a Sterilization Cycle and Rapid Read-out Biological Indicator," which is incorporated herein by reference, enzymes can be identified for a particular type of spore in which the enzyme has particularly useful characteristics that can be exploited to determine the efficacy of a sterilization process.

Exemplary biological indicators suitable for use with the spore carriers of the present disclosure are further described in, e.g., U.S. Pat. Nos. 3,846,242; 4,717,661; 5,073,488; 5,223,401; 5,418,167; 5,739,004; and 5,795,730.

Figure 2:
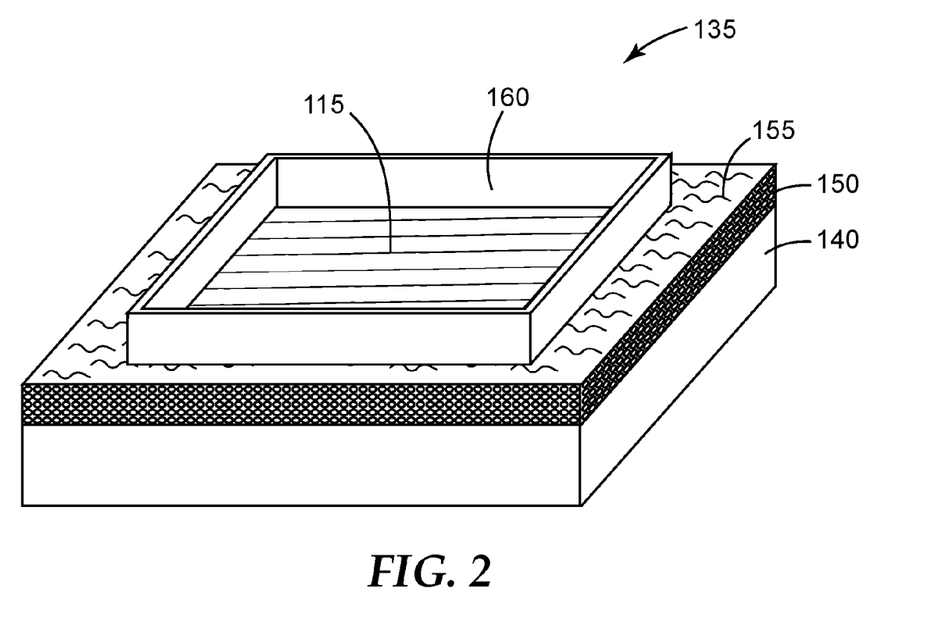
FIG. 2 illustrates an exemplary spore carrier according to some embodiments of the present disclosure.

Spore carrier 135 according to some embodiments of the present disclosure is illustrated in FIG. 2. Spore carrier 135 comprises substrate 140, hydrophilic layer 150 having nanostructured surface 155, and spores 115 bonded to at least a portion of nanostructured surface 155. Optionally, spores 115 may be confined to an area defined by well 160.

Typical spore carrier substrates have included paper, metallic films, and glass. Each presents its own challenges. For example, the substrate should be compatible with the range of sterilization conditions it will be exposed to including high temperatures and exposure to the sterilants themselves. For example a spore carrier substrate made of paper will work with steam as a steriliant but paper is not a suitable spore carrier substrate when hydrogen peroxide is the chosen sterilant because the cellulosic material will retain residual hydrogen peroxide even after the sterilization cycle and thus provide inaccurate biological indicator response. Although such substrates may be suitable for some embodiments of the present disclosure, in some embodiments, polymeric substrates may be used. Exemplary polymeric substrates include polyesters and polyolefins, e.g., polypropylene and polyethylene. In some embodiments, polypropylene substrates may be preferred. In some embodiments, planar sheets of the polymeric substrate may be used. In some embodiments, a textured sheet (e.g., a sheet with random or engineered microstructures may be used. As used herein, microstructures have a maximum cross sectional dimension of greater than 200 nm, e.g., greater than 500 nm and less than 500 microns, e.g., less than 200 microns. In some embodiments, substrates prepared from woven or nonwoven fibers may be used.

In some embodiments, spore carrier 135 may include one or more optional wells 160. Such wells may be integral with or bonded to a surface of substrate 140. Referring to FIG. 2, well 160 is illustrated as raised above the planar surface of substrate 140; however, in some embodiments, wells may be formed as depressions into the substrate. Generally, the materials used to construct the well(s) are not particularly limited, and they may be independently selected from the same or different material(s) used to construct substrate. Generally, the shape and dimensions of the well are not particularly limited. In some embodiments, the walls of the well correspond to or are proximate to the boundaries of the substrate. The resulting spore carrier is approximately "tub-shaped."

While polymer substrates provide several advantages over paper, metal, and glass substrates, several problems have inhibited their use in spore carriers for biological indicators. First, spores may release from the polymeric substrate in a process referred to as flaking. That is, portions of the spore coating break free from the substrate rendering the indicator unsuitable for use in a sterilization application. Second, coating spore solutions on polymeric substrates can be challenging due in part to the generally hydrophobic nature of many common polymers. Thus, when typical aqueous spore-containing compositions are applied, the composition tends to bead-up resulting in a discontinuous, and generally unusable spore coating. Finally, even when a continuous coating can be obtained, multiple layers of spores can be formed. This phenomenon, called clumping, can reduce the reliability of the resulting indicator. For example, some sterilization methods are only partially effective at penetrating into the clumped spore layer. Thus, although efficient sterilization may have occurred, the indicator may indicate a failure as the spores positioned in the lower layers may not have been destroyed.

After discovering many common methods to improve spore coating uniformity and adhesion, such as corona treatment and chemical surface modifiers, were not effective to overcome these deficiencies, the present inventors surprisingly discovered that significant improvements could be achieved using a hydrophilic nanostructured layer. Referring to FIG. 2, hydrophilic nanostructured layer 150 is bonded to substrate 140. In some embodiments, the nanostructured layer is directly bonded to the surface of the substrate. In some embodiments, the nanostructured layer is indirectly bonded to the surface of substrate through one or more intermediate layers, e.g., primer layers. In some embodiments, hydrophilic nanostructured layer 150 may cover the entire surface of substrate 140, or it may be selectively applied to one or more discrete portions of the surface. For example, in some embodiments, the nanostructured layer may be confined to the region proximate well 160, for example, inside the bounds of well 160.

Generally, the hydrophilic nanostructured layer comprises nanoparticles, e.g., inorganic nanoparticles. As used herein, "nanoparticle" refers to a particle having at least one cross-sectional dimension of no greater than 200 nm. In some embodiments, the nanoparticles have an average cross-sectional dimension of no greater than 50 nm, e.g., no greater than 20 nm, e.g., no greater than 10 nm. In some embodiments, microparticles may also be included. Generally, microparticles have cross sectional dimensions greater than 200 nanometers, e.g., 200 nanometers to 50 microns. In some embodiments, microparticles having an average cross sectional dimension of at least 400 nm, e.g., at least 500 nm, may be used. In some embodiments, microparticles having an average cross sectional dimension of no greater than 10 microns, e.g., no greater than 1 micron, or even no greater than 500 nm may be used.

Suitable nanoparticles include silica, calcite, zirconia, titania, and the like, and combinations thereof. In some embodiments, silica nanoparticles may be preferred. Generally, the nanoparticles do not require surface treatments such as covalently bonded surface treatment agents (e.g., silanes). However, in some embodiments, such treated nanoparticles may be used. Inorganic silica sols in aqueous media are well known in the art and available commercially. Silica sols in water or water-alcohol solutions are available, for example, under the trade designations "LUDOX" from E.I. duPont de Nemours and Co., Inc., Wilmington, Del.; "NYACOL" from Nyacol Co., Ashland, Mass.; and "NALCO" from Ondea Nalco Chemical Co., Oak Brook, Ill. One useful silica sol is NALCO 2326 available as a silica sol with mean particle size of 5 nanometers, pH 10.5, and solid content 15% by weight. Other commercially available silica nanoparticles include "NALCO 1115" and "NALCO 1130," commercially available from NALCO Chemical Co., "REMASOL SP30," commercially available from Remet Corp., Utica, N.Y., and "LUDOX SM," commercially available from E.I. DuPont de Nemours Co., Inc.

In some embodiments, generally spherical nanoparticles may be used. As used herein, spherical nanoparticles refers to nanoparticles having an aspect ratio of major dimension to minor dimension of no greater than 1.1. Asphehrical particles (also referred to as acyclical particles), including, e g., ellipsoids and rods, may also be used. Such particles have an aspect ratio of greater than 1.1, e.g., at least 1.5, at least 2, or even at least 5. In some embodiments, such particles, have an aspect ratio of no greater than 50, e.g., no greater than 20. In some embodiments, blends of spherical and aspherical particles may be used. In some embodiments, the ratio of spherical to aspherical particles may range from 10:90 to 90:10, e.g., 20:80 to 80:20.

The resulting layers have a random, nanostructure. This nanostructure may comprise both nanoscale surface roughness as well as nanoscale porosity. Average surface roughness value can be tuned by the addition of microparticles, e.g., a mixture of micro- and nanoparticles at a specific ratio included in the initial composition. The shape of the nanoparticles can be regular or irregular. The porosity of coatings can typically be varied by changing the amount of regular and irregular-shaped nanoparticles in the coatable composition and/or by changing the amount of spherical and aspherical nanoparticles in the coatable composition. In some embodiments, the resulting average surfaces roughness values of the coatings are least 10 nm, e.g., at least 50 nm, e.g., at least 100 nm. In some embodiments, the average surface roughness is no greater than 10 microns, e.g., no greater than 1 micron, or even no greater than 500 nm. The average surface roughness can be expressed by RMS roughness (Rq) values, which can be obtained by atomic force microscopy (AFM) image measurements according to the following equation:

$$Rq = SQRT(\Sigma Z_i^2/N);$$

wherein $Z_i$ is defined as the distance from the measured point to the mean plane of the sample, and where i is the number measurements are made. Generally, the number of measurements required to obtain a statistically significant measure of surface roughness should be made, as would be understood by one of ordinary skill in the art.

The term "porous" refers to the presence of voids between the spherical and/or aspherical nanoparticles created when the particles form a continuous coating. In some embodiments, the nanoparticle coating has a porosity of up to 65 volume percent, in some embodiments, about 15 to 50 volume percent, when dried. In some embodiments the porosity may be higher. Porosity may be calculated from the refractive index of the coating according to published procedures such as in W. L. Bragg, A. B. Pippard, Acta Crystallographica, volume 6, page 865 (1953) incorporated herein by reference. With nanosilica particles, in some embodiments, the nanostructured layer has an index of refraction of 1.15 to 1.40, in some embodiments, 1.20 to 1.36.

In some embodiments, the nanoparticle dispersions may be modified to achieve a low pH, e.g., a pH of less than 5, 4.5, 4, 3.5, 3, or even less than 3. Such aqueous coating compositions can be prepared, for example, by combining at least a dispersion comprising silica nanoparticles and an acid having a lower pH than the dispersion (e.g., an acid having a $pK_a$ of <3.5). Exemplary acids include at least one of oxalic acid, acetic acid, citric acid, hydrochloric acid, and the like; although the selection of the acid is not particularly limited.

In some embodiments, a porous network of silica nanoparticles is obtained by acid sintering of the silica nanoparticles as the water evaporates and the acid concentration increases. As a result of this acid-sintering, the silica particles can deform and bond to adjacent silica particles forming a substantially continuous, porous network. The resulting layer is referred to as acid-sintered.

In some embodiments, the nanoparticle dispersion includes a binder, e.g., an organosilane binder. Suitable binders include, e.g., tetraalkoxysilanes such as tetraethoxysilane (TEOS). In some embodiments, the nanoparticle dispersion may include a surfactant.

EXAMPLES

Materials used in the examples are summarized in Tables 1 and 2.

TABLE 1

Summary of uncoated substrates.

| Substrate | Description | Supplier |
|---|---|---|
| PE | polyethylene copolymer (BYNEL-3101) | DuPont Co., Wilmington, DE |
| PET | Polyethylene terephthalate (MELINEX 618) | DuPont Co. |
| PC | Polycarbonate (LEXAN 8010) | GE Advanced Materials Specialty Film and Sheet; Pittsfield, MA |
| PP1 | biaxially oriented polypropylene | 3M Company, St. Paul, MN |
| PP2 | Polypropylene (TOTAL 3576X), formed into rectangular reservoirs approximately 9 mm × 4 mm × 0.4 mm | Total Petrochemicals USA Inc.; Houston TX |
| PVC | Polyvinyl chloride film 3M(TM) SCOTCHCAL(TM) Luster Overlaminate 8519 | 3M Company |
| PU | polyether-based polyurethane (PELLATHEN 2363) | Dow Chemical, Midland MI |
| Nonwoven 90/10 PP/rayon | Carded nonwoven web: 90% polypropylene/10% rayon | Described below |

*The carded nonwoven web included 90% polypropylene FIBERVISIONS T-133/HY-Entangle 1.7 dtex polypropylene fibers (FiberVisions Corp., Duluth, GA) and 10% LENZING VISCOSE 1.7 dtex, 39 mm cut length, bright raw white rayon rayon fibers (Lenzing Fibers, New York, NY). These fibers were carded through a two roll calendering process at 160° C. with one smooth roll and the other roll with an approximately 17% point bond pattern.

TABLE 2

Summary of colloidal silica dispersions.

| ID | Description | Supplier |
|---|---|---|
| 1115 | NALCO 1115; spherical silica nanoparticle dispersion; 4 nm diameter; 15 wt. % solids; sodium stabilized; pH 10.5 | Nalco Company, Naperville, IL |
| 1030 | NALCO 1030; spherical silica nanoparticle dispersion; 13 nm diameter; 30 wt. % solids; sodium stabilized, pH 10.0 | Nalco Company |
| 1050 | NALCO 1050; spherical silica nanoparticle dispersion; 20 nm diameter; 50 wt. % solids; sodium stabilized, pH 9.0 | Nalco Company |

TABLE 2-continued

Summary of colloidal silica dispersions.

| ID | Description | Supplier |
|---|---|---|
| 2326 | NALCO 2326; spherical silica nanoparticle dispersion; 5 nm diameter; 15 wt. % solids; ammonium stabilized, pH 9 | Nalco Company |
| 8691 | NALCO 8691; spherical silica nanoparticle dispersion; 3-4 nm diameter; 15 wt. % solids; sodium stabilized, pH 10.5 | Nalco Company |
| 8699 | NALCO 8699; spherical silica nanoparticle dispersion; 2-4 nm diameter; sodium stabilized | Nalco Company |
| N004 | NALCO DVSZN004; spherical silica nanoparticle dispersion; 44 nm diameter; 40 wt. % solids ammonium stabilized | Nalco Company |
| OUP | SNOWTEX OUP; 15-16 w. % solids, aspherical silica 9-15 nm diameter; 40-100 nm length; pH 2-4 | Nissan Chemical America Corp., Houston TX |
| UP | SNOWTEX UP; 20-21 wt. % solids, aspherical silica; 9-15 nm diameter; 40-100 nm length; pH 9-10.5 | Nissan Chemical |
| IPA-ST | IPA-ST Organosol(TM); 30-31 wt. % solids, spherical silica 10-15 nm diameter; pH 2-4 | Nissan Chemical |

Dispersion Preparation Procedure. Examples were prepared by diluting the listed colloidal silica nanoparticle dispersions to 5 wt. % total solids (unless otherwise specified) with deionized water and adjusting to approximately pH 2-3 with concentrated aqueous nitric acid (unless an alternative acid was specified). For select examples, a ratio of two or more different colloidal silica nanoparticle dispersions were mixed together in the ratios shown in the following tables, to achieve a final total of 5 wt. %.

Coating Procedure. The indicated substrates were coated using a Meyer bar with a 25 micrometer (1 mil) gap and 5 wt. % total solids silica dispersions, providing a dry coating thickness in the range of 100-200 nm. The coated samples were heated to 80-100° C. for 5 to 10 minutes to effect drying.

Contact Angle Method. Advancing, receding and static water contact angle measurements were made on the dried coated samples using as-received deionized water filtered through a filtration system obtained from Millipore Corporation (Billerica, Mass.), on a video contact angle analyzer available as product number VCA-2500 XE from AST Products (Billerica, Mass.). Reported values are the averages of measurements on at least three drops measured on the right and the left sides of the drops. Drop volumes were 1 microliter (4) for static measurements.

Coating Quality Method. Dispersions that provided a visually uniform coating were designated "Coatable." Coatings that beaded up and/or provided a visually non-uniform coating were designated "Beading."

Coating Stability Method. The coating stability was determined by allowing the dispersion to sit for a period of one month. Those that had no visual separation after a month were considered stable.

Comparative CE-1 and Examples EX-1 to EX-4 were prepared using PP1. This polypropylene substrate was corona treated at a normalized corona energy of 2 Joules per square centimeter prior to being coated with the colloidal silica dispersions. The silica dispersions were prepared according to the Dispersion Preparation Procedure using the nanoparticles identified in Table 3. The substrates were prepared using these dispersions according to the Coating Procedure. The resulting samples tested for static, advancing and receding contact angle (CA) according to the Contact Angle Method. The results are shown in Table 3.

TABLE 3

Contact Angle Measurements for silica coated, corona-treated PP1 substrates.

| Example | Silica dispersion (wt. ratio) | Static CA | Advancing CA | Receding CA |
|---|---|---|---|---|
| CE-1 | None | 76.9 | 79.4 | 67.5 |
| EX-1 | OUP/1115 (7:3) | 7.6 | 7.2 | 0.0 |
| EX-2 | 1115 | 14.8 | 13.7 | 3.6 |
| EX-3 | OUP/1115 (1:1) | 6.7 | 13.2 | 0.0 |
| EX-4 | OUP/1115 (3:7) | 6.2 | 15.8 | 0.0 |

Comparative example CE-2 and Examples EX-5 through EX-16 were prepared as described for EX-1 above except the PET substrate was used instead of the corona treated PP1.

TABLE 4

Contact Angle Measurements for Silica Coated PET Surfaces

| Example | Silica dispersion (wt. ratio) | Static CA | Advancing CA | Receding CA |
|---|---|---|---|---|
| CE-2 | PET | 66.9 | 69.4 | 57.5 |
| EX-5 | OUP/1115 (7:3) | 7.6 | 7.2 | 5.8 |
| EX-6 | 1115 | 14.8 | 12.7 | 8.6 |
| EX-7 | OUP | 4.5 | 8.9 | 8.4 |
| EX-8 | 2326 | 3.5 | 5.4 | 5.5 |
| EX-9 | 1050 | 3.2 | 5.7 | 5.8 |
| EX-10 | OUP/1115 (9:1) | 7.8 | 8.3 | 8.9 |
| EX-11 | OUP/1115 (3:7) | 6.2 | 5.8 | 8.0 |
| EX-12 | OUP/1115 (1:1) | 6.7 | 6.2 | 8.0 |
| EX-13 | OUP/2326 (9:1) | 5.6 | 9.6 | 9.6 |
| EX-14 | OUP/2326 (7:3) | 4.9 | 6.6 | 8.9 |
| EX-15 | OUP/2326 (1:1) | 4.4 | 5.5 | 6.6 |
| EX-16 | OUP/2326 (3:7) | 4.2 | 5.4 | 6.0 |

The effects of coating pH are illustrated in Examples EX-17 through EX-20 and Comparative Examples CE-3 to CE-5. The PET substrate was coated with the indicated nanoparticle dispersions using the procedure described for EX-1. The coated samples were tested for coating quality and contact angle.

TABLE 5

Coating Quality Dependence on pH using dispersions of the UP silica.

| Example | pH | Static CA | Receding CA | Coating Quality |
|---|---|---|---|---|
| EX-17 | 2 | 79.2 | 16.5 | Coatable |
| EX-18 | 3 | 77.9 | 19.6 | Coatable |
| EX-19 | 4 | 80.0 | 19.4 | Beading slightly |
| EX-20 | 5 | 80.6 | 21.7 | Beading slightly |
| CE-3 | 6 | 76.9 | 25.5 | Beading |
| CE-4 | 7 | 79.1 | 49.5 | Beading |
| CE-5 | 10 | 75.8 | 58.1 | Beading |

Dispersions having a pH of 2-3 were prepared using aspherical silica nanoparticles, then coated and dried in the same fashion Example EX-1. As indicated some samples further contained tetraethoxysilane (TEOS, available from Alfa Aesar, Ward Hill, Mass.) and/or spherical silica nanoparticles in the amounts indicated as a weight ratio portion of the 5 wt. % total.

TABLE 6

Contact Angle Measurements

| Example | Additive to aspherical silica (wt. ratio of 5% total solids) | Static Water Contact Angle |
|---|---|---|
| EX-21 | None | 8.5 |
| EX-22 | UP/TEOS (95:5) | 8.2 |
| EX-23 | UP/TEOS (90:10) | 10.1 |
| EX-24 | UP/TEOS (80:20) | 10.3 |
| EX-25 | UP/TEOS (70:30) | 10.3 |
| EX-26 | UP/TEOS (50:50) | 15.6 |
| EX-27 | UOP/TEOS (90:10) | 9.6 |
| EX-28 | OUP/TEOS (70:30) | 11.6 |
| EX-29 | UP/2326 (50:50) | 4.5 |
| EX-30 | UP/1115 (50:50) | 11.4 |
| EX-31 | UP/2326/TEOS (45:45:10) | 11.2 |
| EX-32 | UP/2326/TEOS (40:40:20) | 12.2 |
| EX-33 | UP/2326/TEOS (35:35:30) | 13.2 |

In the following Examples, the PET substrate was coated with the indicated 5 wt. % total solids acicular silica particle dispersions at the indicated pH; prepared, coated and dried as described for Example EX-1. The liquid portion of the coating composition was 79:21 weight ratio of isopropanol/water. The coated samples were tested for Dispersion Stability and Coating Quality using the previously described test methods.

TABLE 7

Properties of Acicular Silica Compositions with IPA/WATER Coated on PET

| Example | Silica dispersion (wt. ratio) | pH | Acid | Dispersion Stability | Coating Quality |
|---|---|---|---|---|---|
| CE-6 | 5 wt. % UP | 10 | None | Precipitate | Not Coatable |
| EX-34 | 5 wt. % UP | 2 | Hydrochloric | Stable | Coatable |
| EX-35 | 5 wt. % UP | 3.5-4.0 | Acetic | Stable | Coatable |

Various substrate materials were coated with the indicated 5 wt. % total solids UP acicular silica particle compositions at the indicated pH; prepared, coated and dried as described in Example EX-1. The coated samples were tested for Contact Angle, Dispersion Stability and Coating Quality using the previously described test methods.

TABLE 8

Contact Angles and Coating Quality for Various Silica Coated Substrates

| Example | Silica Dispersion | pH | Substrate | CA Adv/Rec | Dispersion Stability | Coating Quality |
|---|---|---|---|---|---|---|
| CE-7 | 5 wt. % UP | 10.5 | PET | 77.1/61.5 | Stable | Beads |
| EX-36 | 5 wt. % UP | 2 | PET | 79.2/16.5 | Stable | Coatable |
| EX-37 | 5 wt. % UP | 2-3 | PC | 88.1/31.1 | Stable | Coatable |
| EX-38 | 5 wt. % UP | 2-3 | PU | 104.8/24.2 | Stable | Coatable |
| EX-39 | 5 wt. % UP | 2-3 | PVC | 70.2/16.4 | Stable | Coatable |
| EX-40 | 5 wt. % UP | 2-3 | PE | 80.2/22.2 | Stable | Coatable |

As illustrated in the preceding examples, a wide variety of spore carriers can be prepared according to the present disclosure. Generally, the particular substrate and nanoparticle dispersions can be selected by one of ordinary skill in the art in light of the teachings of the present specification.

Biological Indicator (BI) Examples. Various nanoparticles-coated substrates suitable for use as a spore carrier were tested in actual biological indicators. The BI assembly was a 3M ATTEST Super Rapid Readout Biological Indicator (available from 3M Company, St. Paul, Minn.) with a modified spore carrier using one of the hydrophilic nanostructured substrates described above. As shown in FIG. 1, the biological sterilization indicator 100 included base 104 and cap 106 that were coupled together to provide a self-contained biological sterilization indicator. Cap 106 included six openings 107, which provided fluid communication between reservoir 103 and ambience, for sterilant access. A filter paper material (not shown) which acted as a contamination barrier; was positioned in the sterilant path over apertures 107 and held in place with a pressure sensitive adhesive backed paper label. Frangible container 120 was held in place within biological sterilization indicator 100 by an insert 130. Insert 130 served to both hold the container in place and function to facilitate the controlled breakage of the container, which occurs during an activation step of the BI, when cap 106 is pushed downwards to break frangible container 120 after the BI has been exposed to a sterilization process.

The biological sterilization indicator further included G. stearothermophilus spores 115. The spores were deposited on the hydrophilic (silica nanoparticle) coated PET substrates to form spore carrier 135. Spore carrier 135 was coated and positioned near the bottom of base 104. Following sterilization, the BI's were activated in a 3M ATTEST 490H AUTOREADER biological indicator reading apparatus (available from 3M Company).

Spore carrier films were coated with a 2 microliter drop of Geobacillus stearothermophilus spores (ATCC 7953) and dried. The spore carrier substrates were various polymeric films primed using conventional techniques. In each case, the spore coating flaked and no useable biological indicators could be prepared.

Comparative Examples CE-8 was a corona-treated polypropylene. Examples CE-9 and CE-10 were coated with a diamond-like glass (DLG) coating according to the following process. The diamond-like glass film was deposited in a commercial batch reactor (PLASMATHERM Model 3032), The chamber was pumped by a roots blower (Edwards Model EH1200) backed by a dry mechanical pump (Edwards Model iQDP80). The RF power was delivered by a 5 kW, 13.56 Mhz solid-state generator (RFPP Model RF30S through an impedance matching network. The system had a nominal base pressure of 0.667 Pascal. The flow rates of the gases were controlled by mass flow controllers (MKS Instruments, Inc.). Substrates for deposition were placed on the lower powered electrode.

The samples were then plasma treated in the following manner. The samples were placed on the powered electrode of the batch plasma apparatus. The plasma treatment was done in a series of treatment steps. First, the tips were treated with oxygen plasma by flowing oxygen gas at a flow rate of 750 standard cubic centimeters per minute, pressure of 150 mTorr and plasma power of 300 watts for 30 seconds. After the oxygen plasma treatment, a diamond-like glass film was deposited by flowing tetramethylsilane gas at a flow rate of 50 standard cubic centimeters per minute, oxygen gas at a flow rate of 750 standard cm3/min, pressure of 150 mTorr and plasma power of 300 watts for 30 seconds. The diamond-like glass film was further surface modified by treating in oxygen plasma at a flow rate of 750 cm3/min, pressure of 150 mTorr and plasma power of 300 watts for 60 seconds. After the plasma deposition was completed, the chamber was vented to atmosphere and the samples were removed.

Two non-woven substrates were coated with a 2 microliter drop of *Geobacillus stearothermophilus* spores (ATCC 7953) containing either 0.1% Silwet 77, Union Carbide Corp., Danbury, Conn., or 40% ethanol to improve the wetting of the nonwoven. The coated carriers were dried. Each drop contained greater than $1.0 \times 10^6$ cfu of spores. The spores coated carriers were die-cut to approximately 9 mm×4 mm and assembled into self contained biological indicator (BI) units as described above. Additional check samples of die-cut carrier with spores, prepared in the same manner, were confirmed to have greater than $1.0 \times 10^6$ cfu of spores per die-cut carrier piece.

The resistance of the BIs to hydrogen peroxide was characterized by exposing them to a full hydrogen peroxide sterilization cycles in a STERRAD NX sterilizer, Advanced Sterilization Products a Division of Ethicon Inc., a Johnson & Johnson company, Irvine, Calif. The STERRAD NXsterilizer used two injections of 1.8 mls of 59% hydrogen peroxide in the full cycle. After exposure, the biological indicators were activated by crushing the media ampule and placing in an ATTEST Model 490H Autoreader, 3M Company, St. Paul, Minn. The 490H Autoreaders incubate the indicators at 60° C. and read the fluorescent response of the alpha-glucosidase enzyme produced by the spores after 8 hours of incubation. The indicators continued incubating for 7 days to look for growth of the organism indicated by a pH color change from purple to yellow in the growth medium.

BI performance failure is defined as a fluorescent or growth positive in the full cycle.

TABLE 9

Spore carriers with no nanoparticles coating.

| Example | Substrate Description | Observations | BI Test | CA (Adv/Rec) |
|---|---|---|---|---|
| CE-8 | Corona treated PP2 (no silica coating) | Spore Flaking | Fail | NT |
| CE-9 | DLG* coating on Nonwoven 90/10 PP/rayon | Spore Flaking | Fail | 0* |
| CE-10 | DLG coating on PET with vapor phase deposited aluminum | Spore Flaking | Fail | 45.9/21.6 |
| CE-11 | Nonwoven 90/10 PP/rayon with surfactant | No Flaking | Fail | Not tested |

TABLE 9-continued

Spore carriers with no nanoparticles coating.

| Example | Substrate Description | Observations | BI Test | CA (Adv/Rec) |
|---|---|---|---|---|
| CE-12 | Nonwoven 90/10 PP/rayon with ethanol | No Flaking | Fail | Not tested |
| CE-13 | Unilayer PP spunbond with surfactant | No Flaking | Fail | Not tested |
| CE-14 | Unilayer PP spunbond PP/rayon with surfactant | No Flaking | Fail | Not tested |

*DLG = diamond-like glass

Various colloidal silica compositions (5 wt. % total solids, unless otherwise noted) were coated onto PET film as the spore carrier. These compositions were prepared in the same fashion as described above except that the coating and drying process included using a Yasui Seiki Co., (USA) coater for microgravure reverse kiss coating using a micrograuvure roll #70; max. 18 cm wide/7.6 cm cores/max 28 cm OD rolls; line speed: 3 meters/min, gravure roll (surface) speed: 4.6–6.1 meter/min; oven temp 130° C. in a 3 meter line oven, with an on line wet thickness gauge target set to 8.0+/−1.0 micrometer.

The silica coated PET spore carrier films were coated with a 2 microliter drop of *Geobacillus stearothermophilus* spores (ATCC 7953) and dried. Each drop contained greater than $1.0 \times 10^6$ cfu of spores. The spores coated film carriers were die-cut to approximately 9 mm×4 mm and assembled into self contained biological indicator (BI) units as described above. Additional check samples of die-cut carrier with spores, prepared in the same manner, were confirmed to have greater than $1.0 \times 10^6$ cfu of spores per die-cut carrier piece. None of the samples exhibited spore flaking and each was considered an acceptable spore carrier.

It is important to note that additional BI samples were prepared by directly depositing spores on an uncoated PET film (i.e., no silica coating), but otherwise prepared in exactly the same procedure as described above. All of the examples with spores deposited on an uncoated PET film had such severe spore flaking that the uncoated PET film was considered unsuitable as a spore carrier material. All of the following example that did have the silica coating did not have the spore flaking problem and in that respect were suitable materials.

The resistance of the BIs to hydrogen peroxide was characterized by exposing them to partial hydrogen peroxide sterilization cycles in a STERRAD NX sterilizer, Advanced Sterilization Products a Division of Ethicon Inc., a Johnson & Johnson company, Irvine, Calif. This sterilizer had a manual hydrogen peroxide injection port so different injection volumes of 59% hydrogen peroxide could be tested. The injection volumes ranged from 0.5 to 1.4 milliliters using an exposure time of seven minutes. After exposure, the biological indicators were activated by crushing the media ampule and placing in an ATTEST Model 490H Autoreader, 3M Company, St. Paul, Minn. The 490H Autoreaders incubate the indicators at 60° C. and read the fluorescent response of the alpha-glucosidase enzyme produced by the spores after 8 hours of incubation. The indicators continued incubating for 7 days to look for growth of the organism indicated by a pH color change from purple to yellow in the growth medium.

The silica dispersion composition, sterilization conditions, and positive fluorescence reading (Fl+) and positive growth readings (Gr+) based on 5 or 10 samples prepared at each sterilization condition are summarized below. Generally, it can be desirable for the sterilization indicator to provide a challenging sterilization criteria. Thus, it may desirable for the number of positive fluorescence readings to be no less than the number of positive growth readings. In some embodiments, it may be desirable for the number of positive fluorescence readings to be greater than the number of positive growth readings. This can provided additional confidence that an indicator that does not produce a positive fluorescence reading properly indicates complete sterilization.

TABLE 10

Biological Indicators with Colloidal Silica Coated PET Spore Carrier Films
(Results reported as Fl+/Gr+/Total samples)

| Example | Silica Dispersion | Ratio | 0.5 ml/ 7 min | 0.7 ml/ 7 min | 0.9 ml/ 7 min | 1.1 ml/ 7 min | 1.4 ml/ 7 min | Fl+/Gr+ (total) |
|---|---|---|---|---|---|---|---|---|
| EX-41 | 1115/OUP | 65:35 | 5/2/5 | 2/0/5 | 5/0/10 | 0/0/10 | 1/0/10 | 13/2 |
| EX-42 | 1115/OUP | 70:30 | 5/3/5 | 4/0/5 | 4/0/10 | 0/0/10 | 0/0/10 | 13/3 |
| EX-43 | 8699/OUP | 80:20 | 5/0/5 | 3/0/5 | 2/0/10 | 0/0/10 | 0/0/10 | 10/0 |
| EX-44 | 8691/2326 | 30:70 | 5/0/5 | 2/0/5 | 0/0/10 | 0/0/10 | 0/0/10 | 7/0 |
| EX-45 | N004/8691 | 70:30 | 5/1/5 | 3/0/5 | 6/0/10 | 1/0/10 | 0/0/10 | 15/1 |
| EX-46 | 1115/OUP | 60:40 | 5/1/5 | 5/0/5 | 3/0/10 | 2/0/10 | 0/0/10 | 15/1 |
| EX-47 | 8691/OUP | 10:90 | 5/0/5 | 1/0/5 | 2/0/10 | 1/0/10 | 0/0/10 | 9/0 |

Additional samples were prepared which included various additives in the silica nanoparticles dispersions. DS10 is sodium dodecylbenzene sulfonate, available from Aldrich Chemical Co., Milwaukee, Wis. Fe II refers to weight percent of metal ion added from a 5 wt. % aqueous solution of FeSO4-7H2O compound, available from Sigma-Aldrich of St. Louis, Miss. Again, no flaking was observed for any of the samples.

TABLE 11

Biological Indicators with Colloidal Silica Coated PET Spore Carrier Films
(Results reported as Fl+/Gr+/Total samples)

| Example | Silica Dispersion | Ratio | 0.5 ml/ 7 min | 0.7 ml/ 7 min | 0.9 ml/ 7 min | 1.1 ml/ 7 min | 1.4 ml/ 7 min | Fl+/Gr+ (total) |
|---|---|---|---|---|---|---|---|---|
| EX-48 | 1115/1050 + DS10 | 70:30 | 5/0/5 | 3/0/5 | 1/0/10 | 2/0/10 | 0/0/10 | 11/0 |
| EX-49 | 1115/UP + 5% Fe II 5% solids | 70:30 | 5/0/5 | 3/0/5 | 1/0/10 | 1/0/10 | 0/0/10 | 10/0 |
| EX-50 | 1115/UP + 10% Fe II 7.5% solids | 70:30 | 5/0/5 | 3/0/5 | 1/0/10 | 0/0/10 | 0/0/10 | 9/0 |

Additional spore carriers were prepared using the 90/10 PP/rayon fiber non-woven substrate which were then evaluated as Biological Indicators relative to a flat film substrate. Reference example EX-51 employed PET film and was prepared in the same fashion as previous examples described above with 5 wt. % total solids colloidal silica composition according to Table 12. The nonwoven spore carrier webs were coating in the following manner with the colloidal silica compositions listed in Table 12. Example EX-52, nonwoven A, (NW A) was sprayed coated using an aerosol refillable spray gun, PREVAL, Coal City, Ill. Examples EX-53 and EX-54, nonwovens NW B and NW C, respectively, were coated with a non-aerosol pump spray bottle. Comparative Example CE-15, nonwoven NW D, was not coated with any colloidal silica composition.

The prepared PET and nonwoven spore carrier webs were then loaded with a 2 microliter drop of *Geobacillus stearothermophilus* spores and dried. Each drop contained greater than 1.0×10^6 cfu of spores. The spore coated substrates were die cut and assembled into self contained biological indicator (BI) units as described above. The resistance of the resulting biological indicators was assessed in a similar fashion as described above by exposing them to partial hydrogen peroxide sterilization cycles in the STERRAD NX sterilizer. An injection volume of 1.0 milliliters was used with exposure times of 0.5, 1.0, 1.5, 2.0, 3.0 and 4.0 minutes. After exposure, the biological indicators were activated by crushing the media ampule and placing them in the ATTEST Model 490H Autoreader. The 490H Autoreader incubated the indicators at 60° C. and read the fluorescent response of the alpha-glucosidase enzyme produced by the spores after 8 hours of incubation. The indicators continued incubating for 4 days to look for growth of the organism indicated by a pH color change from purple to yellow in the growth medium. The total number of fluorescent positives (Fl+) and growth positives (Gr+) based on 5 samples for each spore carrier are summarized in Table 12.

TABLE 12

Biological Indicators with Colloidal Silica Coated Nonwoven Spore Carrier Films

| | Example | | | | |
|---|---|---|---|---|---|
| | EX-51 | EX-52 | EX-53 | EX-54 | CE-15 |
| Carrier | PET film | NW A | NW B | NW C | NW D |
| Silica Dispersion | 8691/2326 | 1115/UP | 8691/2326 | 1115/UP | None |
| Ratio | 3:7 | 7:3 | 3:7 | 7:3 | N/A |
| Sterilization | Fl+/Gr+/Total samples | | | | |
| 1.0 mL 0.5 min | 5/5/5 | 5/5/5 | 4/4/5 | 5/5/5 | 5/5/5 |
| 1.0 mL 1.0 min | 5/5/5 | 5/5/5 | 5/5/5 | 5/5/5 | 5/5/5 |

TABLE 12-continued

Biological Indicators with Colloidal Silica
Coated Nonwoven Spore Carrier Films

|  | Example | | | | |
|---|---|---|---|---|---|
|  | EX-51 | EX-52 | EX-53 | EX-54 | CE-15 |
| 1.0 mL 1.5 min | 5/5/5 | 4/4/5 | 5/5/5 | 3/5/5 | 5/5/5 |
| 1.0 mL 2.0 min | 5/5/5 | 2/1/5 | 0/1/5 | 3/0/5 | 5/5/5 |
| 1.0 mL 3.0 min | 1/1/5 | 0/0/5 | 0/0/5 | 0/0/5 | 5/5/5 |
| 1.0 mL 4.0 min | 1/1/5 | 0/0/5 | 0/0/5 | 1/0/5 | 5/5/5 |
| Total Fl+/ Gr+/Tested | 22/22/30 | 16/15/30 | 14/15/30 | 17/15/30 | 30/30/30 |

It is important to note that like CE-15, other BI samples were prepared by directly depositing spores on an uncoated nonwoven substrates (no silica coating). All of the examples with spores deposited on an uncoated nonwoven beaded up and clumped in such a way that the uncoated nonwoven was considered unsuitable as a spore carrier material. In contrast, each of silica coated nonwoven Examples EX-51 through EX-54, when loaded with the spore dispersion, properly dispersed the spores across the nonwoven and did not have any spore flaking problem and thus were considered acceptable spore carrier materials.

Various substrate materials were either treated or untreated with selected coatings as described in Table 13. Unless otherwise noted these examples were prepared, coated and dried in the same fashion as described above. These Examples were tested for suitability as a spore carrier. As described above *G. stearothermophilus* spores were deposited on the various coated and uncoated spore carriers and assessed for spore flaking after drying. Pass criteria were established: the dried down spore coating solution could not flake, spore coating had to be uniform (e.g. spores could not clump which may lead to performance issues), and overall silica coating quality had to be acceptable (no silica flaking). A sample meeting all three criteria was graded as "Pass," and a sample failing even one of these criteria was labeled "Fail." Select examples were also tested for advancing and receding contact angle.

Examples EX-56 through EX-58 were prepared using a dispersion that included DS10 in an amount of approximately 1-2 wt. % of the total weight of silica nanoparticles. Also, these samples were not acidified—the pH was 11. Example EX-59 was prepared from a non-aqueous dispersion of nanoparticles.

TABLE 13

Various Substrates with Surface Treatments Evaluated for Suitable Spore Carriers

| Example | Substrate Description | Spore Flaking | Observations | Pass/Fail | CA Adv/Rec |
|---|---|---|---|---|---|
| EX-55 | Corona treated PP2 + OUP/1115 (7:3) 0.5 wt. % solids | No | Acceptable spore carrier | Pass | 47.1/14.0 |
| CE-16 | PP2 + OUP/1115 (7:3) 0.5% wt. % solids (not corona treated) | No | Silica Flaking | Fail | NT |
| EX-56 | 1115/UP 70:30 (+DS-10; pH = 11) | No | Acceptable spore carrier | Pass | 9.0/0 |
| EX-57 | 1115/UP 50:50 (+DS-10; pH = 11) | No | Acceptable spore carrier | Pass | 8.8/0 |
| EX-58 | 1115/UP 30:70 (+DS-10; pH = 11) | No | Acceptable spore carrier | Pass | 11.6/0 |
| EX-59 | IPA-ST (16 wt. % solids in 100% IPA solvent on PET | No | Acceptable spore carrier | Pass | 13.2/0 |

Various modifications and alterations of this invention will become apparent to those skilled in the art without departing from the scope and spirit of this invention.

What is claimed is:

1. A biological sterilization indicator comprising:
   a housing defining a reservoir, the housing comprising a cap that includes one or more apertures to provide fluid communication between the reservoir and ambience;
   a frangible container within the housing; and
   a spore carrier comprising a substrate, a hydrophilic nanostructured layer bonded to a surface of the substrate and spores bonded to the nanostructured layer, wherein the nanostructured layer comprises silica nanoparticles.

2. The biological sterilization indicator of claim 1, wherein the nanostructured layer has a receding contact angle of no greater than 50 degrees as measured by the Contact Angle Method.

3. The biological sterilization indicator of claim 1, wherein the nanostructured layer has a receding contact angle of no greater than 20 degrees as measured by the Contact Angle Method.

4. The biological sterilization indicator of claim 1, wherein the frangible container contains liquid.

5. The biological sterilization indicator of claim 4, wherein the liquid comprises nutrient medium.

6. The biological sterilization indicator of claim 1, wherein the silica nanoparticles are acid sintered.

7. The biological sterilization indicator of claim 1, wherein the nanoparticles have an average diameter of no greater than 20 nm.

8. The biological sterilization indicator of claim 1, wherein the nanostructured layer has an RMS roughness of at least 10 nm.

9. The biological sterilization indicator of claim 8, the nanostructured layer has an RMS roughness of no greater than 500 nm.

10. The biological sterilization indicator of claim 1, wherein the nanostructured layer further comprises microparticles.

11. The biological sterilization indicator of claim 1, wherein the nanostructured layer further comprises a binder.

12. The biological sterilization indicator of claim 11, wherein the binder comprises a tetraalkoxysilane.

13. The biological sterilization indicator of claim 1, wherein the substrate is a polymeric substrate.

14. The biological sterilization indicator of claim 13, wherein the polymeric substrate comprises polyester.

15. The biological sterilization indicator of claim 13, wherein the polymeric substrate comprises polypropylene.

16. The biological sterilization indicator of claim 1, wherein the substrate is a woven or non-woven web.

17. The biological sterilization indicator of claim 1, wherein the substrate is a film.

18. The biological sterilization indicator of claim 1, wherein the spores comprise at least one of *Geobacillus stearothermophilus* and *Bacillus atrophaeus*.

19. The biological sterilization indicator of claim 1, wherein the spore carrier further comprises one or more wells.

20. The biological sterilization indicator of claim 1, wherein the nanostructured layer comprises silica nanoparticles deposited out of an aqueous coating composition having a pH of less than 3.

* * * * *

UNITED STATES PATENT AND TRADEMARK OFFICE
CERTIFICATE OF CORRECTION

PATENT NO. : 10,059,977 B2
APPLICATION NO. : 15/484781
DATED : August 28, 2018
INVENTOR(S) : Kelvin Witcher et al.

It is certified that error appears in the above-identified patent and that said Letters Patent is hereby corrected as shown below:

In the Specification

Column 3
Line 24, delete "cellibiose," and insert -- cellobiose, --, therefor.
Line 38, delete "bromthymol" and insert -- bromothymol --, therefor.
Line 39, delete "sulfonphthalein" and insert -- sulfonephthalein --, therefor.
Line 44, delete "bromcresol" and insert -- bromocresol --, therefor.
Line 53, delete "bromcresol" and insert -- bromocresol --, therefor.

Column 5
Line 22, delete "steriliant" and insert -- sterilant --, therefor.

Column 6
Line 55, delete "Ondea" and insert -- Ondeo --, therefor.
Line 67, delete "Aspehrical" and insert -- Aspherical --, therefor.

Column 8
Line 45, delete "PELLATHEN" and insert -- PELLETHANE --, therefor.

Column 9
Line 46, delete "(4)" and insert -- (µL) --, therefor.

Column 12
Line 61, delete "3032)," and insert -- 3032). --, therefor.

Column 14
Line 19-20, delete "micrograuvure" and insert -- microgravure --, therefor.

Column 15
Line 29, delete "FeSO4-7H2O" and insert -- FeSO4-7 H2O --, therefor.

Signed and Sealed this
Eighteenth Day of June, 2019

Andrei Iancu
*Director of the United States Patent and Trademark Office*